(12) United States Patent
Janoshazi et al.

(10) Patent No.: US 6,703,212 B1
(45) Date of Patent: Mar. 9, 2004

(54) METHODS AND KITS FOR DIAGNOSING ALZHEIMER'S DISEASE FROM A BLOOD SAMPLE

(75) Inventors: Agnés Janoshazi, Marseillaise (FR); Jean De Barry, rue Ganzau (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/463,692

(22) PCT Filed: Jul. 27, 1998

(86) PCT No.: PCT/FR98/01660

§ 371 (c)(1),
(2), (4) Date: Mar. 13, 2000

(87) PCT Pub. No.: WO99/06590

PCT Pub. Date: Feb. 11, 1999

(30) Foreign Application Priority Data

Jul. 25, 1997 (GB) .............................................. 9715815

(51) Int. Cl.$^7$ ................................................. C12Q 1/48
(52) U.S. Cl. ..................... 435/15; 435/69.2; 435/968; 435/975
(58) Field of Search .................... 435/15, 968, 69.2, 435/69.7, 975

(56) References Cited

U.S. PATENT DOCUMENTS

| | | | |
|---|---|---|---|
| 4,874,694 A | * | 10/1989 | Gandy et al. .................. 435/15 |
| 6,107,050 A | * | 8/2000 | Alkon et al. .................. 435/7.4 |
| 6,197,928 B1 | * | 3/2001 | Tsien et al. .................. 530/350 |
| 6,218,113 B1 | * | 4/2001 | Yue et al. ....................... 435/6 |
| 6,369,086 B1 | * | 4/2002 | Davis et al. ................. 514/338 |
| 6,511,800 B1 | * | 1/2003 | Singh ............................ 435/4 |
| 2001/0009764 A1 | * | 7/2001 | Grammas et al. ............ 435/7.1 |

FOREIGN PATENT DOCUMENTS

| | | | |
|---|---|---|---|
| WO | WO 93/04194 | | 3/1993 |
| WO | WO 97/07402 | | 2/1997 |
| WO | WO 97/11094 | | 3/1997 |
| WO | WO 99/06590 | * | 2/1999 |

OTHER PUBLICATIONS

Chen C. New Fluorescent Probes for Protein Kinase C. J of Biological Chemistry 268(21) 15812–15822, 1993.*
Matsushima H. Platelet Protein Kinase C Levels in AD. Neurobiology of Aging 15(16)671–674, 1994.*
Bosman G. Are Thrombocyte Membranes Altered in AD. Neurobiology of Aging 13(6)711–716 1992.*
Masliah E. Protein Kinase C Alteration is an Early Biochemical Marker in AD. J of Neuroscience 11(9)2759–2767 1991.*
Masliah, et al., "Protein Kinase C Alteration is an Early Biochemical Marker in Alzheimer's Disease," *J. of Neuroscience*, 11(9) 2759–2767 (1991) XP 002046527.
Krafft, et al., "Fluorescent Probes in Studies of Proteases," ACS Symposium Series–Fluorescent Chemosensors For Ion And Molecule Recognition, vol. 538, pp 1183–1195 (1993) XP 002062970.

* cited by examiner

*Primary Examiner*—Ralph Gitomer
(74) *Attorney, Agent, or Firm*—Foley & Lardner

(57) ABSTRACT

The invention relates to methods for diagnosing Alzheimer's disease from a blood specimen. The method involves incubating a blood sample with a fluorescent probe that interacts with either protein kinase C (PKC) or protein kinase A (PKA), and measuring the fluorescence intensity in different conditions. Variation in the emission spectra data relative to those of the spectra obtained with healthy subjects is a discriminatory factor vis-à-vis Alzheimer's disease. The probes may recognize the catalytic site or the regulator domain of PKC or PKA, and may be coupled to a synthetic organic compound such as bis-indolmaleimide. In one aspect, the probes are lipidic, including probes prepared from phospholipid constituents of a cell membrane. In another aspect, the probes are proteinic or peptide probes of a membrane or cytoskeletal nature. Useful probes include derivatives of substrates for PKC or PKA.

14 Claims, 6 Drawing Sheets

METHODS AND KITS FOR DIAGNOSING ALZHEIMER'S DISEASE FROM A BLOOD SAMPLE

CROSS-REFERENCES TO RELATED APPLICATIONS

This application is a national stage filing of PCT/FR98/01660, filed Jul. 27, 1998, under 35 U.S.C. §371. This application also claims priority based on French application no. 97 09823, filed Jul. 31, 1997.

A subject of the invention is a method and kits for diagnosing Alzheimer's disease.

The general increase in longevity favours the frequency with which Alzheimer's disease occurs and this pathology constitutes a major economic problem for modern societies. A significant research effort has been carried out in order to understand the genesis of this disease, but attempts to find an early marker have been unsuccessful or incomplete. Clinical examination is most frequently used alone and certain diagnosis is only made after cerebral biopsy or autopsy.

Recently, an American team proposed the use of cholinergic antagonists in the measurement of pupil dilation as a screening test (Scinto et al., 1994, Science 266: 1051–1054). However, this test does not allow the absolute discrimination of patients suffering from Alzheimer's disease. Its diagnostic use has been brought into question in several more recent studies.

Finally, it has also been shown recently that serum originating from patients suffering from Alzheimer's disease contains antibodies capable of recognising antigens expressed by the microglial cells of mice. The reasons for this property and its diagnostic value have not been established for the moment.

The observation of various anomalies in patients suffering from Alzheimer's disease has led the inventors to study the relationships between these anomalies and modifications to the activation levels of certain enzymes.

Therefore, taking into account the relationships previously established between a chloride transport anomaly in erythrocytes, in patients suffering from Alzheimer's disease and an anomaly in the activity of protein kinase C (abbreviated to PKC), their work has at first been carried out on measurement of the activation level of PKC in the erythrocytes of such patients.

The inventors then noted that by varying the measurement conditions, it was possible to make available data which allows the discrimination of patients suffering from the disease form healthy subjects.

Development of their work allowed verification of such measurements applied to PKA, or also using a set of compounds capable of interacting with PKC or PKA, which can also be used to discriminate patients suffering from Alzheimer's disease.

Therefore, an aim of the invention is to provide a method for diagnosing Alzheimer's disease which allows a reliable test to be established, which is rapid and of low cost.

It also aims to provide kits which allow an easy implementation of such a method.

BRIEF SUMMARY OF THE INVENTION

The method for diagnosing Alzheimer's disease according to the invention is characterized in that it includes:
- the incubation of a blood sample with one or more fluorescent probes under conditions which allow a specific bond between the probe or probes with PKC or PKA, and
- measurement of the fluorescence intensity of the preparation obtained and its possible variations by the addition of inhibitor or activator of said enzyme, a variation in the emission spectra data relative to those of the spectra obtained with healthy subjects, being a discriminant vis-à-vis Alzheimer's disease.

DETAILED DESCRIPTION OF THE INVENTION

Figure 1:
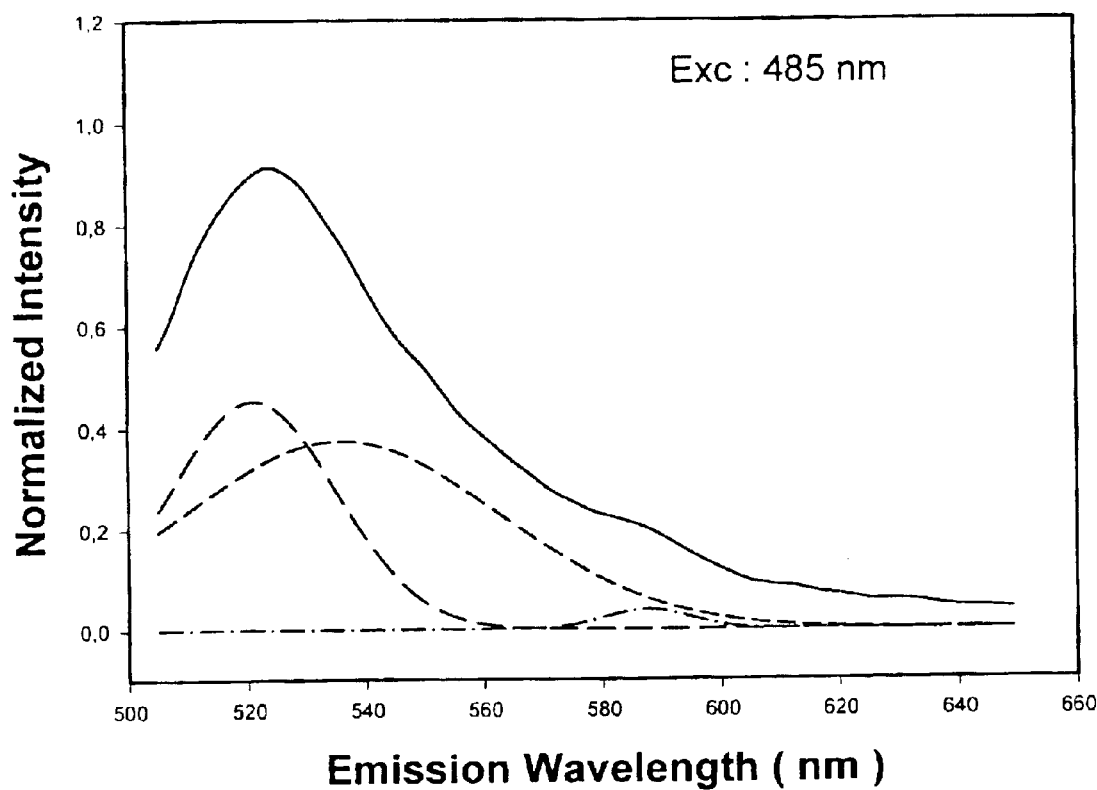
FIG. 1 represents the deconvolution of the emission spectrum of fim-1.

According to the invention, in order to study the fluorescence intensities a deconvolution of the emission spectra obtained is carried out in order to break them down into elementary gaussian distributions and to determine the emission peaks characteristic of the interaction, direct or indirect, of the probe with PKC or PKA. Determination of the relative contribution of each gaussian distribution to the overall fluorescence intensity under different conditions, allows the selection of criteria to be retained to make the diagnosis. For example, it is the difference in the relative intensity or a peak shift relative to the results obtained with healthy subjects.

Therefore, means are available which allow a 100% discrimination to be established between patients suffering from Alzheimer's disease and healthy patients.

The fluorescent probes which can be used in the method according to the invention comprise, coupled with a fluorophore, a compound capable of interacting, under the incubation conditions, respectively with the catalytic site of the enzyme, or its regulator domain, when the corresponding probes are used.

The fluorescent probes capable of reacting, under the conditions of the invention, with the catalytic site of PKC, comprise synthetic organic compounds, such as derivatives of bis-indolmaleimide. In particular the probes fim-1 and rim-1 described by Chen and Poenie in J. Biol. Chem, 1993, 268, 15812–15822 can be mentioned.

According to an embodiment of the invention, in addition fluorescent probes are used capable of reacting, under the conditions of the invention, with the regulator domain of PKC.

In particular they are lipidic probes, as prepared from phospholipid constituents of the membrane, or derivatives of such phospholipids.

As a variant, the fluorescent probes are proteinic or peptide probes of a membrane or cytoskeletal nature, or derivatives of substrates of PKC or PKA enzymes.

Such lipidic, proteinic or peptide probes are used simultaneously with the probes recognising the catalytic domain of the PKC enzymes. In this way the specificity of the measurements is ensured, enzymes or proteins other than PKC or PKA being capable of interacting with the lipidic, proteinic or peptide compounds of the probes.

These probes comprise for example compounds which ensure an emission in the excitation domain of the probes interacting with the catalytic domain of the enzymes.

Their excitation leads in its turn to that of the probe recognizing the catalytic site, which implies a proximity of the two probes (less than approximately 50 Å), the enzyme then interacting directly with the elements of the membrane or cytoskeleton or substrate.

Thus, by exciting the sample to be studied at the absorption wavelength of the lipidic probe and by observing the signal at the emission wavelength of the catalytic probe, a specific signal is available vis-à-vis the enzyme and allows the discrimination to be established.

By "blood sample" is meant the total sample taken from the patient or a fraction of this sample, or constitutive elements, for example erythrocytes.

In a general manner, for the implementation of the method according to the invention, a sample of fresh blood is used.

The incubation stage is carried out at ambient temperature, by loading the sample to be studied with a quantity of probe, and according to the duration, allowing the desired interaction to be obtained.

In a preferred embodiment of the invention, one part of the sample is incubated with the probe or probes alone, another part is firstly incubated with an inhibitor of PKC or PKA, then with the probe or probes and another part is incubated beforehand with an activator of PKC or PKA, then with the probe or probes.

By way of example, staurosporine can be mentioned as an inhibitor of PKC, and a phorbol ester such as phorbol myristate acetate (PMA or TPA) can be mentioned as an activator.

The deconvolution of the spectra obtained allows the characteristic peaks of interactions to be identified. Comparison of the spectra in the presence or not of an activator and or an inhibitor of the enzyme allows variations to be revealed in patients suffering from Alzheimer's disease compared with healthy patients and a clear discrimination between these groups to be rapidly established.

The invention also relates to diagnostic kits or sets for the implementation of the test defined above. These kits are characterized in that they comprise, with instructions for use, the fluorescent probe or probes as defined above, with, if appropriate, receptacles and reagents, these reagents being chosen from activators and/or inhibitors of PKC and/or PKA. As a variant, the kits according to the invention comprise at least one set of 2 fluorescent probes, one recognising the catalytic site of PKC or PKA, the other its regulator domain.

Therefore, the invention provides means off high reliability which are non-invasive, allowing the rapid and economical diagnosis of Alzheimer's disease to be carried out.

By developing computer tools for the analysis of the spectra recorded, it is possible to very rapidly carry out measurements on significant groups of subjects who are likely to develop the disease and on families certain members of which show hereditary forms.

EXAMPLE 1

Study of the Fluorescence Properties of Fim-1.

Liposomes prepared from lipidic extracts of brain and a commercial preparation of purified a PKC are used, then erythrocytes are added.

This preparation is incubated for 20 minutes at ambient temperature, in the presence of fim-1 (500 nM) in a PBS buffer (150 mM NaCl, 10 mM $NaHPO_4$, 5 mM D-glucose, 500 μm $CaCl_2$, pH 7.4.

After washing, centrifugation and resuspension in PBS 1/150, the fluorescence emission spectrum is recorded between 505 and 450 nm, with an excitation wavelength of 485 nm.

The spectrum obtained is standardized relative to the fluorescence intensity measured with the probe alone, then broken down into the 3 elementary gaussian distributions represented in FIG. 1. An emission maximum is noted at 518, 535 and 586 nm respectively. The interactions between fim-1 and the membrane lipids as well as the PKC is expressed by a slight shift of the spectrum between 530 and 70 nm for the lipids and an increase in fluorescence between 510 and 530 nm, and beyond 570 nm for the PKC.

The addition of staurosporine competitive inhibitor of the ATP site, is expressed by an inhibition in the fluorescence intensity on the other hand, a considerable increase in fluorescence (the quantal yield increases by a factor of 5000) is noted in the presence of phorbol ester.

EXAMPLE 2

Diagnostic Test for Alzheimer's Disease Protocol 1 to 3 ml of fresh blood is taken on heparin and stored in the cold (+4° C.). Over the following two hours the sample is washed and centrifuged three times in PBS at ambient temperature.

Then 3 incubation series are carried out:

a first aliquot of cells is incubated for 20 minutes in the presence of the fluorescent probe (500 nM) fim-1, a second aliquot first pre-incubated in the presence of 500 nM of staurosporine for 20 minutes then in the presence of the fluorescent probe, and a third aliquot first pre-incubated in the presence of the fluorescent probe then 500 nM of TPA for 20 minutes.

Following these incubations the cells are washed, centrifuged (twice), then resuspended in PBS (1/150).

The respective fluorescence emission spectra are measured with a volume of approximately 200 μl with a single-beam SLM 4800 spectrofluorimeter (Ex 485 nm, slot width 2 nm), at ambient temperature. Each measurement is taken three times at least in duplicate, then an average of the values is established.

The spectra are then standardized relative to the fluorescence intensity measured with the probe alone, then broken down into 3 elementary gaussian distributions. The integral of each gaussian distribution is finally measured and related to the sum of the integrals of the gaussian distributions for each spectrum (relative contribution of each gaussian distribution to the overall fluorescence intensity).

Discrimination Between Alzheimer's Patients and Healthy Subjects

Figure 2:
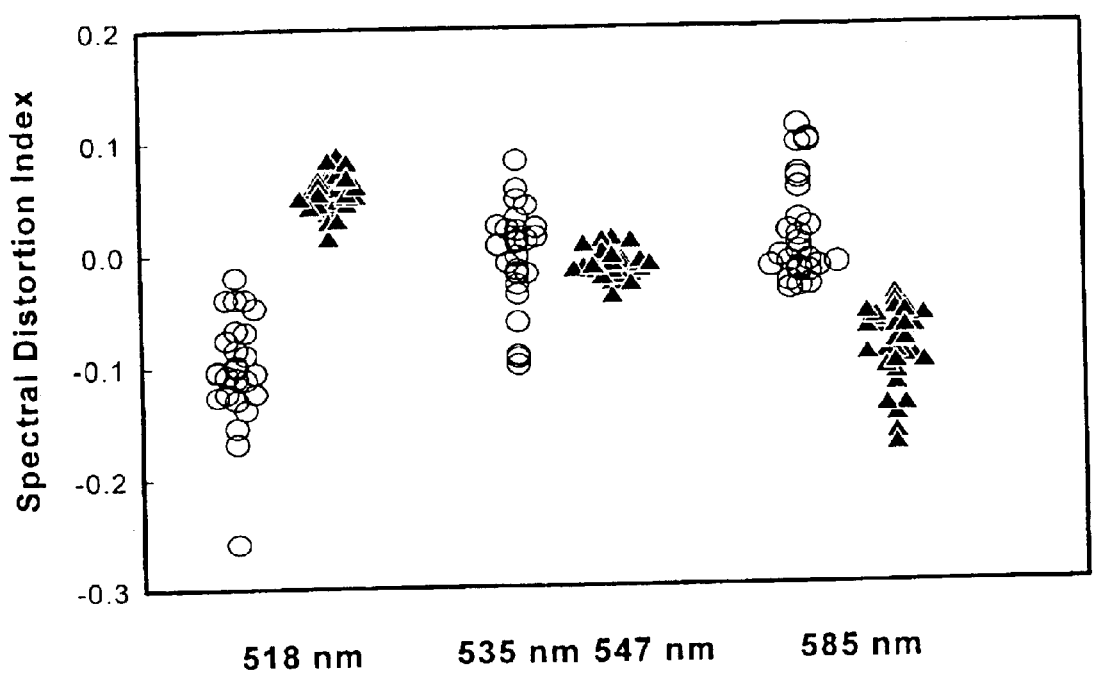
FIG. 2 shows the differences in relative fluorescence intensity emission peaks at 518, 535, 547 and 585 nm of preparations of erythrocytes pre-incubated with staurosporine, then with fim-1 added.
Figure 3:
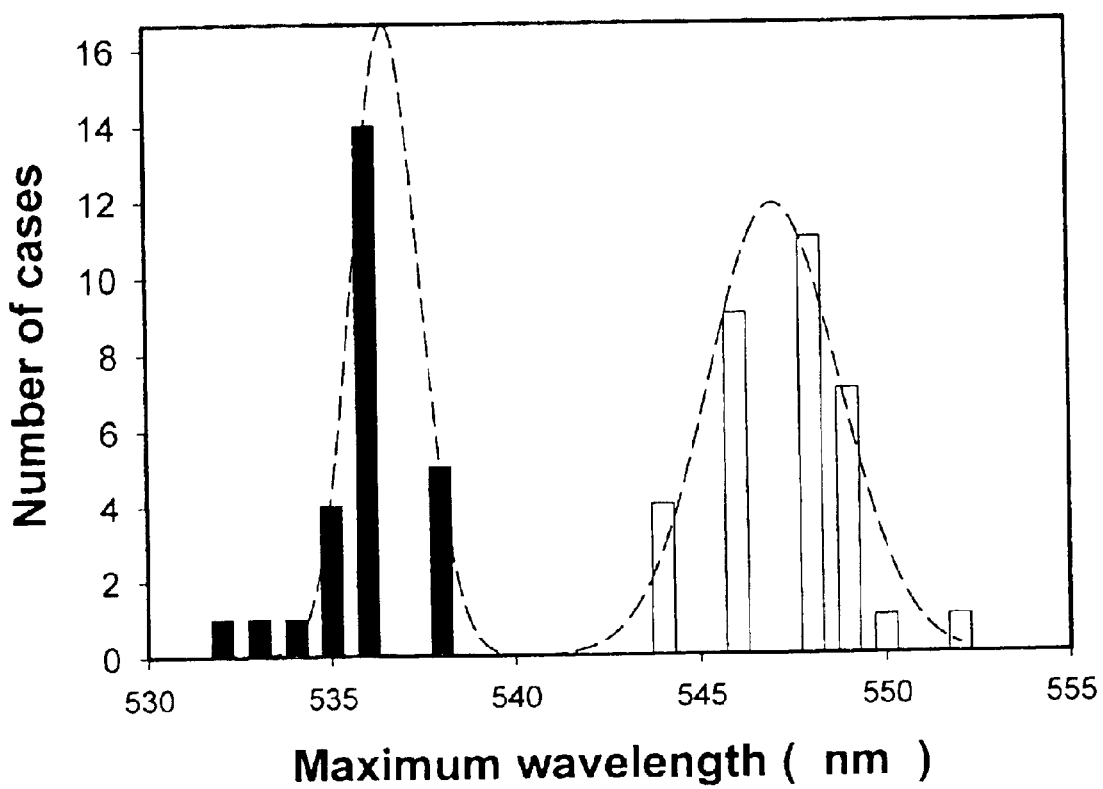
FIG. 3 shows the shift of the second peak by comparing the samples of Alzheimer's patients and healthy volunteers.

Measurement of the fluorescence emission spectra of fim-1 in red blood cells originating from 35 patients suffering from Alzheimer's disease and their comparison with those obtained from 35 healthy volunteers of a comparable age allowed a 100% discrimination between the 2 groups using 2 criteria: the difference in intensity of the fluorescence peak at 518 nm when the spectrum is measured in the presence or in the absence of staurosporine (FIG. 2), and the maximum shift of the peak at 545 nm.

Figure 4:
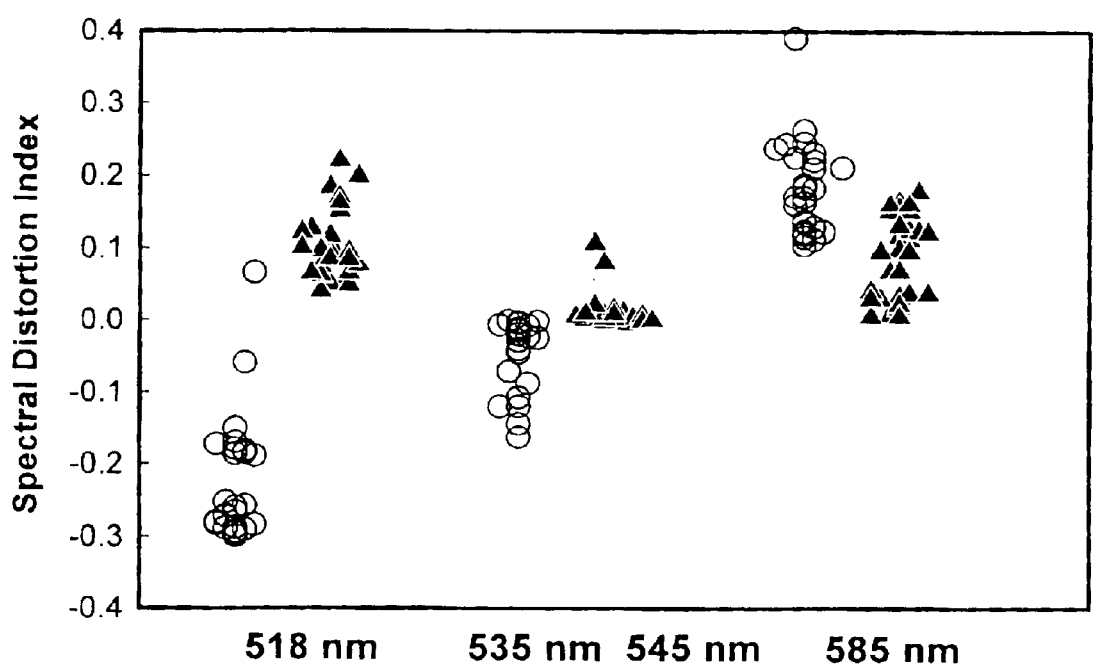
FIG. 4 shows the differences in relative fluorescence intensity emission peaks at 518, 535, 545 and 585 nm of preparations of erythrocytes pre-incubated with fim-11, then with TPA added.

In these figures ▲ and ■ correspond to Alzheimer's patients and ○ and □ to healthy patients. These symbols have the same meanings in FIG. 4 which represents the results obtained in the presence or in the absence of phorbol ester.

Measurements Made on Patients Suffering From Parkinson's Disease

Figure 5:
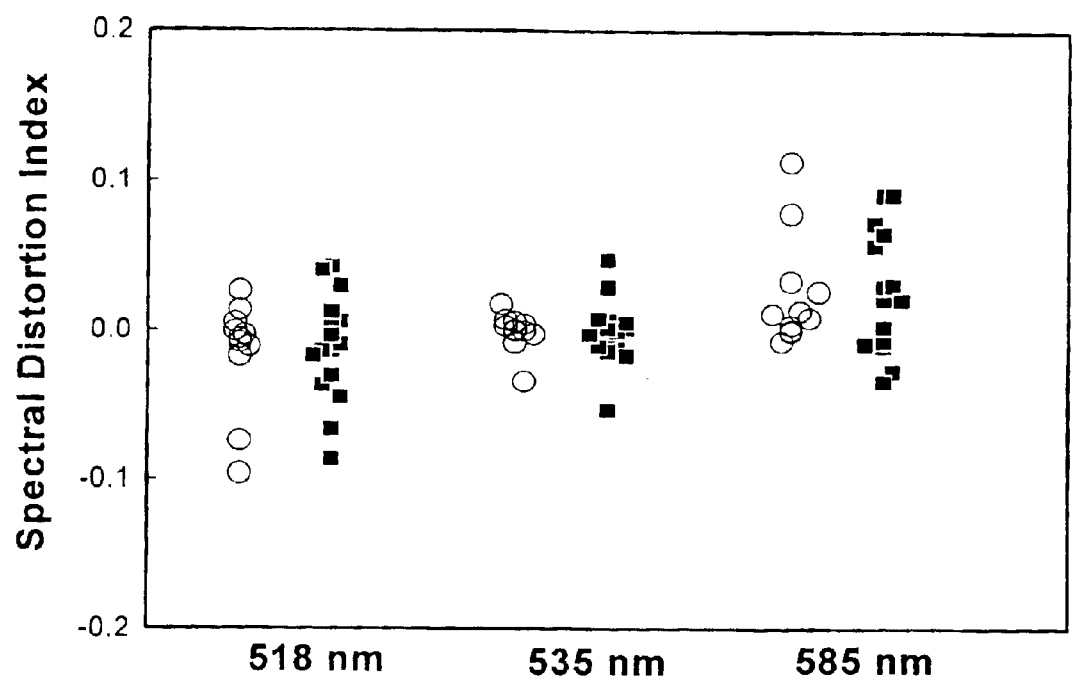
FIGS. 5 and 6 show the differences in relative fluorescence intensity emission peaks of preparations of erythrocytes from healthy patients and patients suffering from Parkinson's disease, pre-incubated with staurosporine, then with fim-1 added (FIG. 5), or pre-incubated with fim-1, then with TPA added (FIG. 6).
Figure 6:
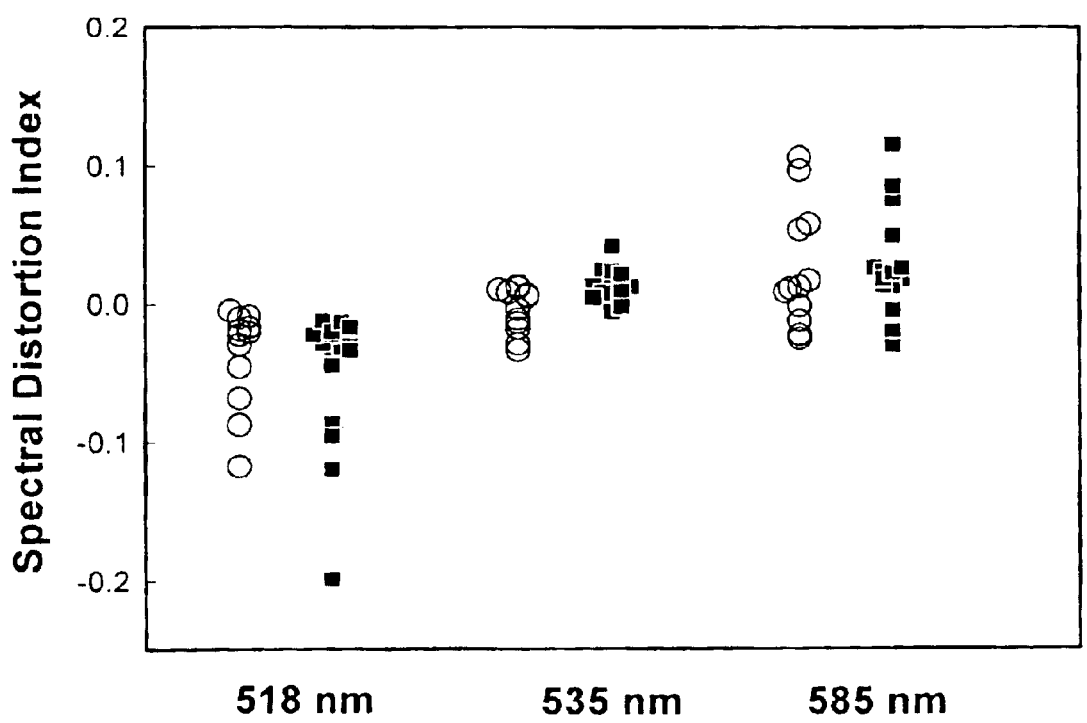

So as to establish the specificity of the measurements for Alzheimer's disease compared to other neurodegenerative diseases, measurements were taken with samples orginating from 15 patients suffering from Parkinson's disease or healthy volunteers of comparable age. The two measurement indicators retained did not allow the difference between the healthy volunteers and the patients to be observed (effect of staurosporine: FIG. 5 and effect of TPA: FIG. 6 where "○" corresponds to healthy volunteers and "▲" to Parkinson's patients. This result is a good indicator of the specificity of the test according to the invention for the diagnosis of Alzheimer's disease.

What is claimed is:

1. A method for diagnosing Alzheimer's disease, comprising measuring fluorescence emission spectra of a blood sample from a patient, said blood sample having been incubated with (i) a fluorescent probe recognizing a catalytic site of protein kinase A (PKA), or (ii) a fluorescent probe recognizing a catalytic site of protein kinase C (PKC), or (iii) two fluorescent probes respectively recognizing a catalytic site and a regulator domain of PKA, or (iv) two fluorescent probes respectively recognizing a catalytic site and a regulator domain of PKC, said fluorescence emission spectra being measured in the presence and absence of an inhibitor or activator of said PKA or PKC; wherein a variation in said fluorescence emission spectra relative to fluorescence emission spectra obtained from healthy subjects is a diagnostic indicator for Alzheimer's disease.

2. The method of claim 1, wherein each fluorescent probe comprises a fluorophore coupled to a compound that interacts with the respective catalytic site or regulator domain of said PKC or PKA.

3. The method of claim 2, wherein said compound is a synthetic organic compound.

4. The method of claim 3, wherein said synthetic organic compound is a bis-indolmaleimide derivative.

5. The method of claim 3, wherein said blood sample has been incubated with a fluorescent probe recognizing a catalytic site of PKC.

6. The method of claim 5, wherein said probe or probes are lipidic.

7. The method of claim 6, wherein said lipidic probe or probes are prepared from phospholipid constituents of a cell membrane, or derivatives of such phospholipids.

8. The method of claim 5, wherein said probe or probes are proteinic or peptide probe(s) of a membrane or cytoskeletal nature.

9. The method of claim 5, wherein said probe or probes are derivatives of substrates of PKC.

10. The method of claim 5, wherein said blood sample has been simultaneously incubated with two fluorescent probes respectively recognizing a catalytic site and a regulator domain of PKC.

11. The method of claim 1, wherein said blood sample has been incubated with said probe or probes at ambient temperature.

12. A method for diagnosing Alzheimer's disease, comprising:

(a) incubating one part of a blood sample with (i) a fluorescent probe recognizing a catalytic site of protein kinase C (PKC), or (ii) a fluorescent probe recognizing a catalytic site of protein kinase A (PKA), or (iii) two fluorescent probes respectively recognizing a catalytic site and a regulator domain of PKC, or (iv) two fluorescent probes respectively recognizing a catalytic site and a regulator domain of PKA, under conditions that allow specific probe binding, to obtain a first preparation;

(b) incubating a second part of said sample with one or more inhibitors of said PKC or PKA, then with said probe or probes under conditions that allow specific probe binding, to obtain a second preparation;

(c) incubating a third part of said sample with said probe or probes under conditions that allow specific probe binding, then with one or more activators of said PKC or PKA, to obtain a third preparation;

(d) measuring fluorescence emission spectra of each preparation;

wherein a variation in said fluorescent emission spectra relative to fluorescent emission spectra from healthy subjects is a diagnostic indicator for Alzheimer's disease.

13. A kit for diagnosing Alzheimer's disease, comprising:

(a) one or more fluorescent probes selected from the group consisting of (i) a fluorescent probe recognizing a catalytic site of protein kinase C (PKC), (ii) a fluorescent probe recognizing a catalytic site of protein kinase A (PKA), (iii) two fluorescent probes respectively recognizing a catalytic site and a regulator domain of PKC, and (iv) two fluorescent probes respectively recognizing a catalytic site and a regulator domain of PKA, (b) at least one additional component selected from the group consisting of (i) activators of PKC, (ii) inhibitors of PKC, (iii) activators of PKA, and (iv) inhibitors of PKA, (c) instructions for performing a blood test for Alzheimer's disease.

14. A kit according to claim 13, wherein said fluorescent probes are two fluorescent probes respectively recognizing a catalytic site and a regulator domain of PKC, or two fluorescent probes respectively recognizing a catalytic site and a regulator domain of PKA.

* * * * *